United States Patent
Schanze et al.

(10) Patent No.: US 7,214,543 B2
(45) Date of Patent: May 8, 2007

(54) METHOD AND APPARATUS FOR SENSING NITROAROMATICS

(75) Inventors: Kirk S. Schanze, Gainesville, FL (US); James M. Boncella, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 470 days.

(21) Appl. No.: 10/271,671

(22) Filed: Oct. 15, 2002

(65) Prior Publication Data

US 2003/0100123 A1      May 29, 2003

Related U.S. Application Data

(60) Provisional application No. 60/329,070, filed on Oct. 12, 2001.

(51) Int. Cl.
*G01N 21/76* (2006.01)

(52) U.S. Cl. .................. 436/172; 436/164; 422/82.01; 422/82.06; 422/82.08

(58) Field of Classification Search ............... 436/149, 436/150, 151, 164, 169, 170, 173; 422/82.01, 422/52.05, 82.06, 82.07, 82.08
See application file for complete search history.

(56) References Cited

U.S. PATENT DOCUMENTS

| | | | | |
|---|---|---|---|---|
| 4,334,880 A | * | 6/1982 | Malmros | 435/7.4 |
| 5,156,810 A | * | 10/1992 | Ribi | 422/82.01 |
| 5,247,190 A | * | 9/1993 | Friend et al. | 257/40 |
| 5,622,872 A | * | 4/1997 | Ribi | 436/518 |

(Continued)

FOREIGN PATENT DOCUMENTS

| WO | WO 99/57222 | 11/1999 |
|---|---|---|
| WO | WO 00/66790 | 11/2000 |

OTHER PUBLICATIONS

Tsuchihara, et al. "Tractable Silicon-Containing Poly(diphenylacelylenes): Their Synthesis and High Gas Permeability" J. Am. Chem. Soc. 1991, 113, pp. 8548-8549.

Tsuchihara, et al. "Polymerization of Silicon-Containing Diphyenylacetylenes and High Gas Permeability of the Product Polymers" Macromolecules, 1992, 25, pp. 5816-5820.

(Continued)

*Primary Examiner*—Jill Warden
*Assistant Examiner*—Dwayne K. Handy
(74) *Attorney, Agent, or Firm*—Akerman Senterfitt

(57) ABSTRACT

The subject invention pertains to a method and apparatus for sensing nitroaromatics. The subject invention can utilize luminescent, for example fluorescent and/or electroluminescent, aryl substituted polyacetylenes and/or other substituted polyacetylenes which are luminescent for sensing nitroaromatics. In a specific embodiment, the subject invention can utilize thin films of fluorescent and/or electroluminescent aryl substituted polyacetylenes and/or other substituted polyacetylenes which are fluorescent and/or electroluminescent. In a specific embodiment, the fluorescence from thin films of fluorescent, substituted polyacetylene, such as—poly-[1-phenyl-2-(4-trimethylsilylphenyl)ethyne] (PT-MSDPA) is strongly quenched by the vapors of a variety of nitroaromatic compounds present at levels ranging from parts-per-million to parts-per-billion in air.

26 Claims, 6 Drawing Sheets

U.S. PATENT DOCUMENTS

| | | | |
|---|---|---|---|
| 6,025,462 | A | 2/2000 | Wang et al. |
| 6,251,690 | B1 * | 6/2001 | Kulmala et al. ............ 436/518 |
| 6,331,438 | B1 * | 12/2001 | Aylott et al. ................ 436/172 |
| 6,589,731 | B1 * | 7/2003 | Chen et al. ..................... 435/5 |
| 6,680,206 | B1 * | 1/2004 | McDevitt et al. ........... 436/172 |

OTHER PUBLICATIONS

Teraguchi, et al. "Polymerization of Diphenylacelylenes Having Very Bulky Silyl Groups and Polymer Properties" J. Polym. Sci A: Polym. Chem. 36, 1998, pp. 2721-2725.

Yang, et al. "Fluorescent Porous Polymer Films as TNT Chemosensors: Electronic and Structural Effects" J. Am. Chem. Soc. 1998, 120, pp. 11864-11873; and.

Grone, et al. "Detection of Landmines by Amplified Fluorescence Quenching of Polymer Films: A Man-Portable Chemical Sniffer for Detection of Ultra-Trace Concentrations of Explosives Emanating from Landmines" Nomadics, Inc., 1730 Cimarron Plaza, Stillwater, OK 74075, pp. 1-10.

Miao, et al., "Fluorescence Sensory Polymers Containing Rigid Non-planar Aromatic Scaffolds," Papers Presented at the American Chemical Society, 39:1081-1082, 1998.

Liu et al., "Fluorescent Polyacetylene Thin Film Sensor for Nitroaromatics," The American Chemical Society, 17:7452-7455, 2001.

* cited by examiner

PTMSDPA

US 7,214,543 B2

METHOD AND APPARATUS FOR SENSING NITROAROMATICS

CROSS-REFERENCE TO RELATED APPLICATION(s)

The present application claims the benefit of U.S. Provisional Application Serial No. 60/329,070, filed Oct. 12, 2001, which is hereby incorporated by reference herein in its entirety, including any figures, tables, nucleic acid sequences, amino acid sequences, or drawings.

The subject invention was made with government support under a research project supported by Defense Advanced Research Projects Agency (grant # DAAD 19-00-1-0002).

BACKGROUND OF INVENTION

Conjugated polymers have received considerable attention as the active materials in fluorescence-based chemical sensors because of their high sensitivity to a variety of solution- and vapor-phase analytes. The response characteristics of a thin-film polymer fluorescence sensor depend strongly on a number of factors including the permeability of the analyte in the polymer, and the strength of the chemical (or physical) interaction between the analyte and the photoactive polymer, where permeability (P) is the product solubility (S) and diffusivity (D) of an analyte in a polymer, i.e., P=S*D. Recently, it has been demonstrated that by using a sterically demanding pentiptycene moiety it is possible to increase the permeability of a highly fluorescent poly(phenyleneethynylene) film thereby increasing the response of the material to vapor-phase analytes. The bulky pentiptycene moiety is believed to create molecular-scale channels which provide pathways for the analyte molecules to diffuse into the polymer and readily interact with the electron-rich π-conjugated system. The resulting increase in permeability of the pentiptycene-substituted poly(phenyleneethynylene) film can allow the analyte to quench the polymer's fluorescence more rapidly and efficiently compared to similar polymers that lack the sterically-demanding pentiptycene group. Others have demonstrated that doping a surfactant into a film of a fluorescent conjugated polyelectrolyte considerably improves the film's response to neutral analyte molecules. The surfactant is believed to improve the fluorescence response by increasing the solubility (sorption) of the neutral analyte in the film.

BRIEF SUMMARY

The subject invention pertains to a method and apparatus for sensing nitroaromatics. The subject invention can utilize luminescent, for example fluorescent and/or electroluminescent, aryl substituted polyacetylenes and/or other substituted polyacetylenes which are luminescent for sensing nitroaromatics. In a specific embodiment, the subject invention can utilize thin films of fluorescent and/or electroluminescent aryl substituted polyacetylenes and/or other substituted polyacetylenes which are fluorescent and/or electroluminescent. In a specific embodiment, the subject invention involves a method of using the disubstituted polyacetylene PTMSDPA to detect the presence of nitroaromatic vapors. The subject invention also relates to nitroaromatic vapor sensors incorporating fluorescent and/or electroluminescent aryl substituted polyacetylenes and/or other substituted polyacetylenes which are fluorescent and or/electroluminescent. In a specific embodiment, the subject nitroaromatic sensor can utilize disubstituted polyacetylene PTMSDPA thin films. The subject thin films can exhibit fluorescence that is strongly quenched by nitroaromatic vapors. Alternatively, the subject thin films can exhibit electroluminescence created by the application of an electric field across the thin film. In this case, the electroluminescence can be quenched by exposure of the thin films to the target nitroaromatic compound.

In addition, the subject thin films can be used as the active material in a device, for example a diode type device, which produces an electrical signal, wherein exposure of the active material to the target nitroaromatic compound alters the electrical signal of the device. Preferably, the electrodes of such a device would allow the ambient atmosphere to reach the active material. For example, porous electrodes, interdigitated electrodes, or electrodes having channels can be used.

In another embodiment, particles of the fluorescent aryl substituted polyacetylenes or other fluorescent substituted polyacetylenes can be positioned in an environment to be tested and appropriate light shone on the particles such that particles located near a source of nitroaromatic compound, for example a landmine, would not fluoresce to the degree of particles not near such sources or nitroaromatic compounds. Preferably, the subject films or particles have thicknesses or mean diameters of less than 100 nm. The physical mechanism for the quenching process is believed to involve CT complexes that are formed, for example, between the nitroaromatic acceptors and the electron rich PTMSDPA polymer chain. PTMSDPA has a unique combination of properties, including high vapor permeability and strong fluorescence, which are valuable for use in optical sensors. Sensors in accordance with the subject invention can detect the presence of nitroaromatic vapors upon the quenching of photoluminescence, for example fluorescence and/or electroluminescence produced by films or particles of disubstituted polyacetylene PTMSDPA.

DETAILED DISCLOSURE

Figure 1A:
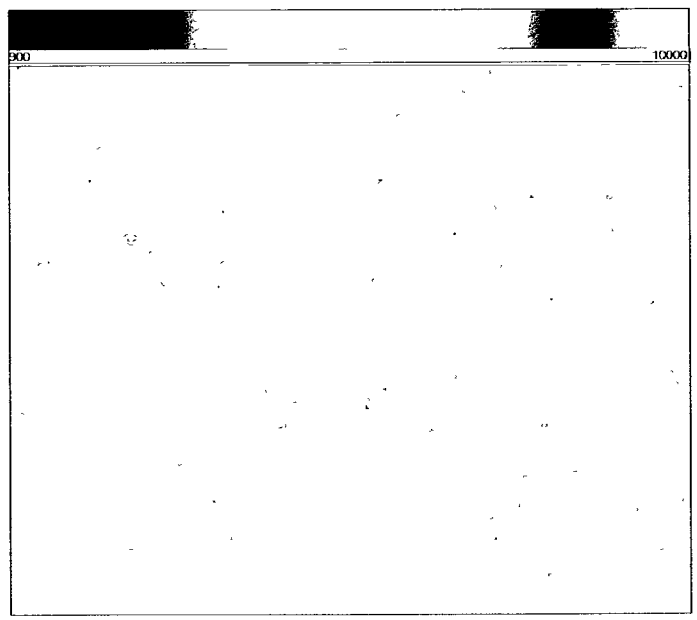
FIG. 1A shows a fluorescence microscope image of a 7 nm thick PTMSDPA film having an image size of 385×308 µm, where white scale bar is 100 µm long and color scale ranges from 900–10,000 counts.

The subject invention pertains to a method and apparatus for detecting nitroaromatic compounds. A specific embodiment of the subject invention can utilize changes in the luminescence emitted from luminescent aryl substituted polyacetylenes and/or other luminescent substituted polyacetylenes to detect the presence of nitroaromatics. In a further embodiment, the subject invention can utilize changes in the luminescence emitted from fluorescent aryl substituted polyacetylenes and/or other fluorescent substituted polyacetylenes to detect the presence of nitroaromatics. In another specific embodiment, the subject invention can utilize changes in electroluminescence emitted from electroluminescent aryl substituted polyacetylenes and/or other electroluminescent substituted polyacetylenes to detect the presence of nitroaromatics preferably, substituted polyacetylenes with large gas permeability are used. Examples of polymers which can be utilized with the subject invention include poly-(1-trimethylsilylpropyne) (PTMSP) and poly-[1-phenyl-2-(4-trimethylsilylphenyl)ethyne] (PTMSDPA). PTMSP has the highest fractional free volume (0.29) and gas permeability of all known polymers, while PTMSDPA displays exceptionally high permeability and high fractional free volume (0.26). In addition to being highly permeable, like many other bis-aryl substituted polyacetylenes PTMSDPA is strongly fluorescent. In a specific embodiment, PTMSDPA can be used in the fabrication of a thin-film and/or particle based fluorescent sensor for vapors of neutral analytes. Nitroaromatic compounds are weakly volatile and are strong quenchers of the fluorescence of electron rich chromophores. The detection of nitroaromatic vapors can include the detection of 2,4,6-trinitrotoluene (TNT) and 2,4-dinitrotoluene (DNT), as these materials are the primary constituents of the explosives used in many land mines.

The luminescent aryl substituted polyacetylenes and/or other luminescent substituted polyacetylenes utilized in accordance with the subject invention can have a variety of shapes, such as thin films, particles, and/or fibers. In specific embodiments, the thin films, particles, and/or fibers utilized in accordance with the subject invention can have thicknesses, mean diameters, and mean diameters of less than about 1 μm, respectively. In a further specific embodiment, the thicknesses, mean diameters, and mean diameters of the thin films, particles, and/or fibers can be less than about 100 nm, respectively. In a further specific embodiment, the thicknesses, mean diameters and mean diameters of the thin films, particles, and/or fibers, can be less than about 10 nm, respectively.

Various excitation sources can be utilized to cause the photoluminescent aryl substituted polyacetylenes and/or other luminescent substituted polyacetylenes to luminesce, for example to fluoresce and/or electroluminesce. Such excitation sources can include, for example, lasers, LED's, and electrodes to apply a voltage across the electroluminescent material, and/or other excitation sources known in the art.

Various means for monitoring the luminescence emitted from the luminescent aryl substituted polyacetylene and/or other luminescent substituted polyacetylense can be used, such as a human eye, photomultiplier, solid state detector, charge coupled device (CCD), or other photodetecting means known in the art.

The polyacetylenes utilized in the methods and devices in the subject invention can be substituted, for example, with an aromatic or heteroaromatic moiety, or with a chemical group that contains an aromatic or heteroaromatic moiety. In a specific embodiment, the polyacetylenes utilized in accordance with the subject invention can be substituted, for example with a moiety selected from the group consisting of: aryloxycarbonyl arylcarbonyloxy, heteroaryl-oxycarbonyl, and heteroarylcarbonyloxy each of which is, optionally, substituted with $C_{1-10}$ alkyl, CN, COOH, $NO_2$, $NH_2$, $SO_{2-4}$, $C_{1-20}$ heteroalkyl, $C_{2-20}$ alkenyl, alkynyl, akynyl-aryl, alkynyl-heteroaryl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, OH, $NH_2$, CN, $NO_2$, COOH, or $SO_{2-4}$.

In other embodiments, the substituted carboxylic group can be substituted with a moiety selected from the group consisting of $C_{1-10}$ alkyl, CN, COOH, $NO_2$, $NH_2$, $SO_{2-4}$, $C_{1-20}$ heteroalkyl, $C_{2-20}$ alkenyl, alkynyl, akynyl-aryl, alkynyl-heteroaryl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, OH, $NH_2$, CN, $NO_2$, COOH, or $SO_{2-4}$. Exemplary heterocyclic groups include, but are not limited to, morpholine, triazole, imidazole, pyrrolidine, piperidine, piperazine, pyrrole, dihydropyridine, aziridine, thiazolidine, thiazoline, thiadiazolidine, and thiadiazoline.

Figure 4:
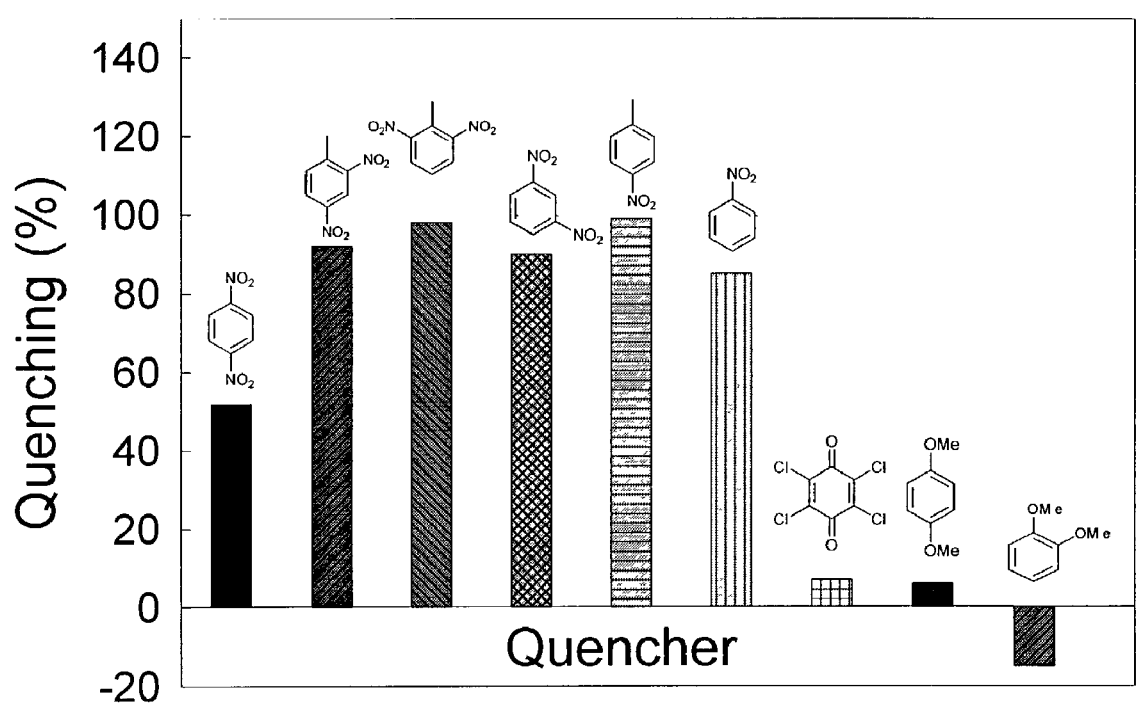
FIG. 4 illustrates fluorescence quenching (% decrease of the initial intensity) of 3 nm PTMSDPA films by various analytes, where quenching % was determined after the film was exposed to the analyte vapor for 20 min at 298 K.

Vapor-phase nitroaromatic compounds can quench the fluorescence of thin films of PTMSDPA when PTMSDPA thin films are exposed to such vapor-phase nitroaromatic compounds. FIG. 4 illustrates the quenching results of a series of nitroaromatics which can quench the fluorescence of PTMSPDPA strongly and selectively. The nitroaromatics addressed in FIG. 4 include 1,4-dinitrobenzene, 2,4-dinitrotoluene, 2,6-dinitrotoluene, and 1,3-dinitrobenzene. The nitroaromatic quenching phenomenon is believed to arise from charge transfer (CT) complex formation between the electron-rich PTMSDPA backbone and the electron poor nitroaromatic. The rapid response of the material is clearly related to its high permeability and fractional free volume which allows the vapor phase nitroaromatic molecules to penetrate into the film rapidly.

In a specific embodiment, PTMSDPA can be produced by a variety of methods. PTMSDPA can be, for example, synthesized by polymerization of 1-phenyl-2-(4-trimethylsilylphenyl)ethyne, which can be prepared according to the procedure described in Tsuchihara, K.; Masuda, T.; Higashimura, T. *J. Am. Chem. Soc.* 1991, 113, 8548–8549, which is incorporated herein by reference. Polymerization can be carried out by use of a variety of catalysts, for example with a $TaCl_5$/n-$Bu_4Sn$ catalyst as described in Tsuchihara, K.; Masuda, T.; Higashimura, T. *Macromolecules* 1992, 25, 581–5820; and in Teraguchi, M.; Masuda, T. *J. Poly. Sci. A Poly. Chem.* 1998, 36, 2721–2725, both of which are incorporated herein by reference.

PTMSDPA can be synthesized by polymerization of 1-phenyl-2-(4-trimethylsilylphenyl)ethyne using a $TaCl_5$/n-$Bu_4Sn$ catalyst in accordance with the Tsuchihara K.; Masuda T.; Higashimura, T. *J. Am. Chem. Soc.* (1991) 113, 8548–8549, and Tsuchihara, K.; Masuda, T.; Higashimura, T. *Macromolecules* 1992, 25, 5816–5820 (1992), which are herein incorporated by reference. The molecular weight of PTMSDPA produced in this way was determined on a Rainin Dynamax HPLC that was equipped with two PLgel 5 μm Mixed-D size exclusion columns (300×7.5 mm, Polymer Labs) and a UV absorbance detector operating at 260 nm. The GPC was calibrated using polystyrene standards (Polymer Laboratories). Films of PTMSDPA were spin-cast from toluene solution onto borosilicate glass microscope cover slides at a spin rate of 2000 rpm. The films were dried under vacuum at room temperature overnight before the experiments were carried out. The concentration of the PTMSDPA/toluene solution was adjusted to vary the film thickness. A concentration of 0.7 mg-mL$^{-1}$ produced a film of 3 nm thickness. The thickness of the ultrathin films was estimated by measuring the film's absorbance at 425 nm. The absorbance versus thickness calibration plot was constructed by measuring the absorbance of films of known thicknesses ranging from 50–100 nm. The thickness of these films was determined by profilometry on a Dektak 3030 profilometer. Atomic Force Microscopy (AFM) was performed under ambient conditions with a Nanoscope III (Digital Instruments, Santa Barbara, Calif.) operating in tapping mode using silicon nitride tips. The fluorescence microscope system consisted of an inverted microscope platform (Olympus, model IX 70) fitted with a 100 W Hg source (USH-102DH) and a CCD camera (Princeton, RTE 1300×1030) mounted to the side port. Fluorescence microscopy was conducted with a blue-violet modular filter cube (Chroma Technology, excitation 425 nm, 40 nm bandpass; 475 nm dichroic splitter). The fluorescence emission was imaged through a 475 nm long pass filter (Chroma Technology).

Fluorescence spectra were measured on a SPEX Fluorolog-2 or on a spectrometer consisting of an ISA-SPEX Triax 180 spectrograph equipped with a LN2 cooled CCD detector (Hamamatsu CCD, 1024×64 pixels). During fluorescence measurements the polymer films were contained in sealed quartz cuvettes. For quenching studies, the solid analyte was added at time=0 and then the cuvette was sealed to allow the solid-vapor equilibrium to be established. Fluorescence spectra were recorded at intervals after addition of the analyte. Absorption spectra were obtained on a Cary-100 UV-visible spectrometer. Fluorescence lifetimes were measured using a PRA time-correlated single photon counting instrument that used a 405 nm pulsed laser diode with 800 ps pulse width (nano-LED, IBH Co., Glascow, UK) as an excitation source and the fluorescence wavelength was selected by using a 550 nm (10 nm bandwidth) interference filter.

PTMSDPA can be synthesized by polymerization of 1-phenyl-2-(4-trimethylsilylphenyl)ethyne using a TaCl$_5$/n-Bu$_4$Sn catalyst. The polymerization reaction is facile and proceeds in high yield making it possible to produce multigram quantities of PTMSDPA in one polymerization reaction. GPC analysis of the PTMSDPA sample produced in this way indicate that the material has $M_n$=293,000 (PDI=1.6). The polymer has good solubility in THF, toluene and chlorinated hydrocarbons, and solutions can be cast to form films having outstanding mechanical properties (indeed, free-standing films of the material can be easily prepared).

Figure 1B:
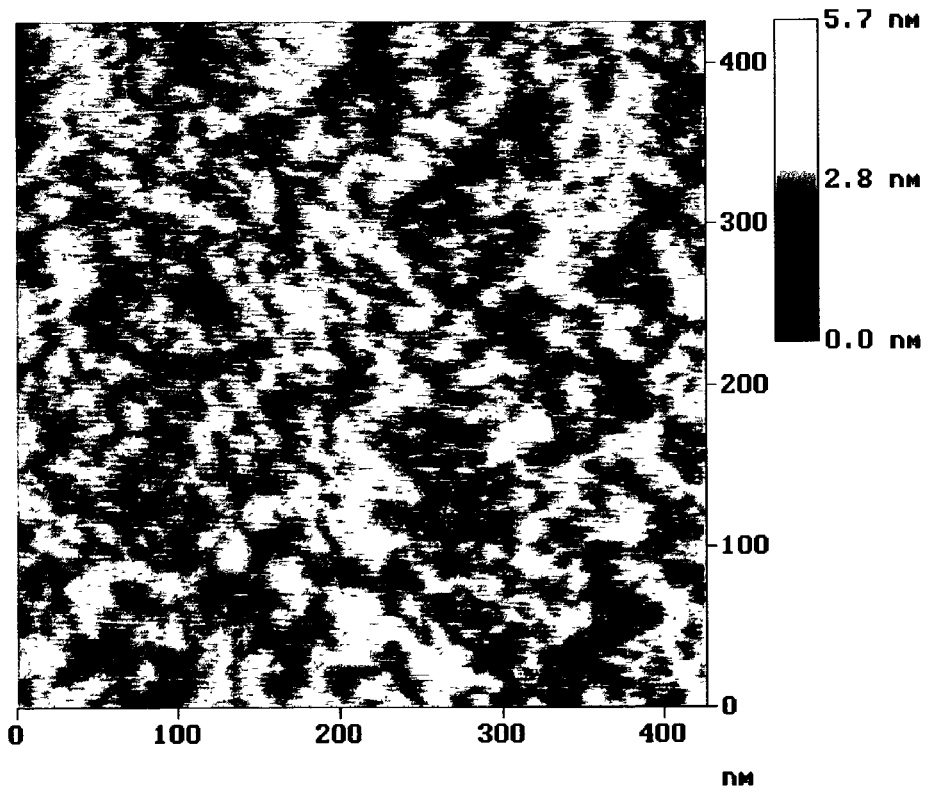
FIG. 1B shows an AFM image of a 7 nm thick PTMSDPA film having an image size of 450 nm×450 nm.

As noted above, previous studies demonstrate that PTMSDPA is highly permeable to light gases (i.e., N$_2$, O$_2$ and H$_2$) and hydrocarbon vapors. The high permeability has been ascribed to the polymer's large fractional free volume and interconnected "channels" that allow small molecules to rapidly diffuse within the matrix. In order to explore the morphology of ultrathin films of PTMSDPA similar to those used in the fluorescence sensor work described below, we used fluorescence microscopy and tapping-mode AFM to image the surface of 7 nm thick films of the polymer that were spin-coated from toluene. FIG. 1A illustrates a fluorescence microscope image of a typical region of the film (385×308 μm). The image is quite uniform—with the exception of a few point defects, the film features a very homogeneous fluorescence intensity. Thus, on the length scale accessible with optical microscopy the PTMSDPA films are uniform. In order to examine the film morphology with higher spatial resolution we examined the same film using tapping mode AFM. A typical AFM image of a PTMSDPA film is illustrated in FIG. 1B; analysis of this image reveals that the surface exhibits an RMS roughness of 0.5 nm. The AFM imaging experiments indicate that spin-coated films of PTMSDPA feature a continuous but somewhat "porous" structure having a length scale on the order of 10–20 nm. The porous surface morphology that is imaged by AFM may reflect the relatively porous structure of the polymer bulk that is caused by the inability of the rigid polyacetylene chains to pack in the solid. This porous structure allows the bulk of the film to equilibrate rapidly with vapor-phase analytes (see below).

In toluene solution PTMSDPA (c=50 μM) features absorption bands at 430 nm ($\epsilon$=4630 M$^{-1}$cm$^{-1}$) and 370 nm ($\epsilon$=4440 M$^{-1}$cm$^{-1}$, $\epsilon$ values computed based on repeat unit molecular mass) and a broad fluorescence band with $\lambda_{max}$=520 nm. The polymer's fluorescence is relatively efficient ($\phi$=0.25) and very short-lived ($\tau$<50 ps). These features are very characteristic of bis-aryl substituted polyacetylenes. The low-energy absorption band of a 7 nm thick film of PTMSDPA is slightly blue-shifted from its solution value ($\lambda_{max}^{film}$=423 nm) and the fluorescence is slightly red-shifted ($\lambda_{max}^{film}$=533 nm). These features are consistent with the existence of interchain aggregates in the solid material. Nevertheless, the fluorescence from the polymer film is very strong and it is easily detected by eye when the material is illuminated with a 7 W near-UV handlamp.

Figure 2A:
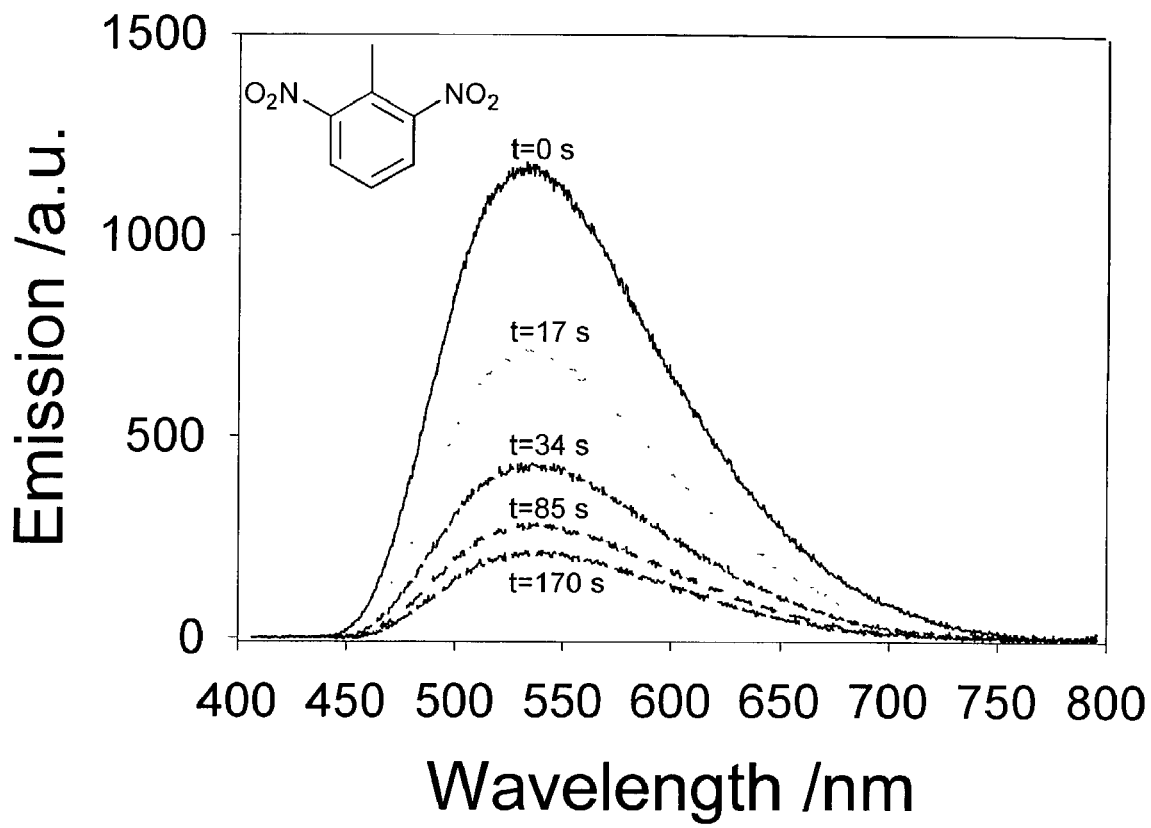
FIG. 2 shows the fluorescence from a 7 nm thick PTMSDPA film at various times following introduction of solid 2,6-DNT to the fluorescence cuvette, where the inset shows the fluorescence intensity as a function of exposure time.
Figure 2B:
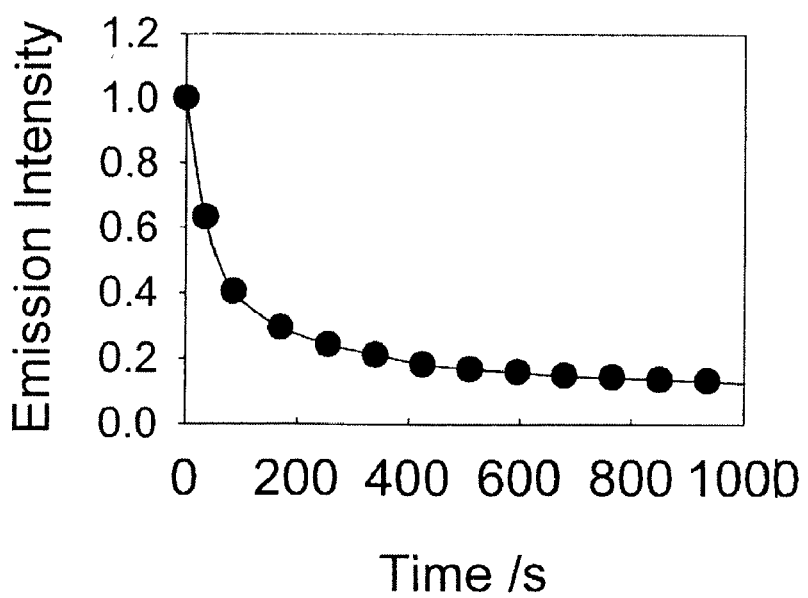

FIG. 2 illustrates fluorescence spectra of a 7 nm thick spin-cast PTMSDPA film as a function of time following the addition of a crystal of solid 2,6-dinitrotoluene (2,6-DNT) to the cuvette containing the film. This data shows that the PTMSDPA fluorescence intensity decreases significantly with increasing time of exposure to the 2,6-DNT. As shown in the inset of FIG. 2, the fluorescence intensity drops quickly within the first 2 minutes after addition of 2,6-DNT and then it decreases more slowly until attaining stable value that is ≈10% of the unquenched intensity. The rate by which the film's fluorescence is quenched is apparently determined by the sublimation rate of the 2,6-DNT and/or by the rate at which the vapor of the analyte permeates into the polymer film. The fluorescence maximum and bandshape is unchanged in the presence of the 2,4-DNT, which indicates that the interaction between the electron poor nitroaromatic and the electron rich polyacetylene does not afford emissive (exciplex) states. Although the quenching is reversible, the fluorescence recovers more slowly than the quenching develops. For example, a 3 nm thick film that had been exposed to 2,6-DNT exhibited >90% recovery of the initial fluorescence intensity when it was allowed to stand in air for approximately 1 hr. The recovery time can be decreased by purging with dry N$_2$ gas. For example, the 90% recovery time was decreased to approximately 10 min when the sample was placed in a vial that was being gently purged with dry N$_2$ gas.

Figure 3:
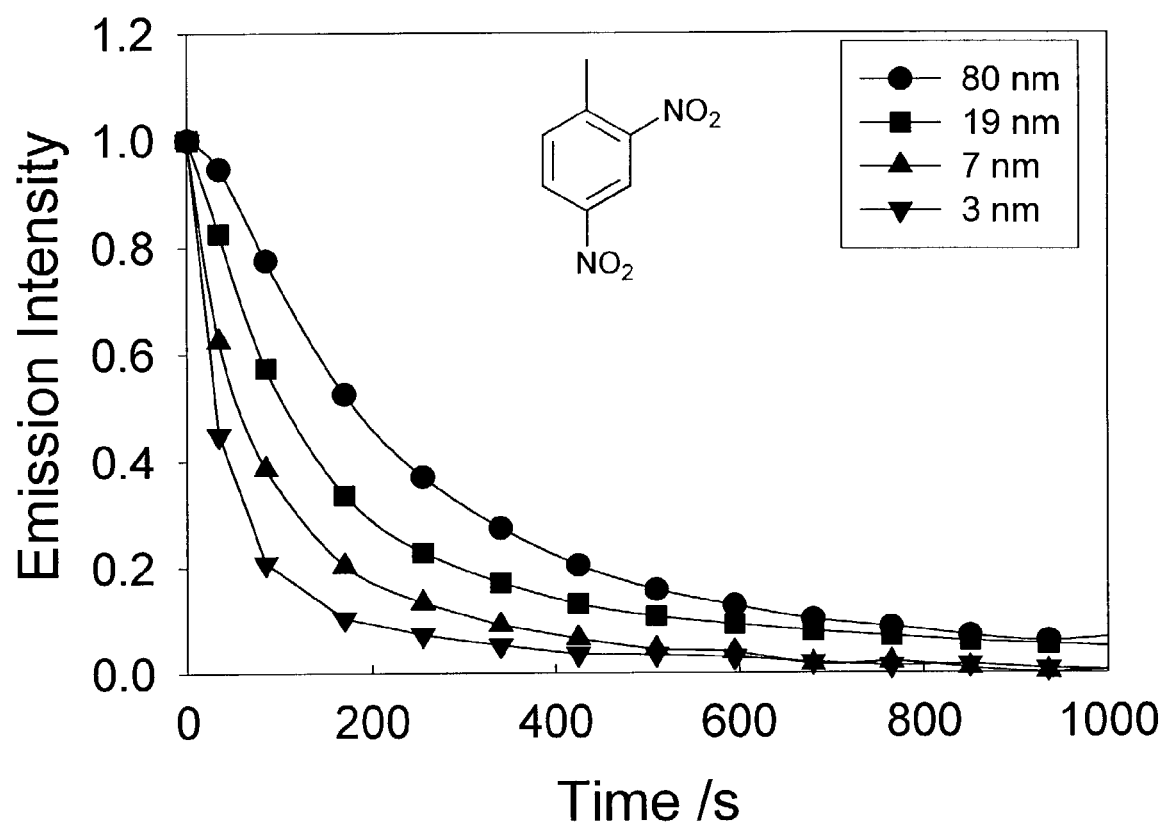
FIG. 3 shows PTMSDPA fluorescence intensity as a function of exposure time to 2,4-DNT vapor, where the legend indicates the thickness of the PTMSDPA films.

The fact that the rate by which the nitroaromatic permeates into the conjugated polymer film is important in determining the rate of the fluorescence quenching process is established by a study of the quenching of a series of PTMSP films of varying thickness by 2,4-dinitrotoluene (2,4-DNT). FIG. 3 illustrates the influence of film thickness on the rate at which 2,4-DNT quenches the PTMSDPA fluorescence. It is clear that the rate of the quenching process increases with decreasing film thickness. For an 80 nm thick film, the fluorescence decreases to 50% of its initial value in≈200 s (i.e., $t_{50\%}$=200 s); however, for a 3 nm thick film the 50% quenching level is reached in less than 20 s ($t_{50\%}$=20 s).

Assuming that the sublimation rate is the same in the four 2,4-DNT quenching rate measurements, then it appears that the parameter responsible for the observed difference in fluorescence quenching arises from the effect of film thickness on the rate by which the nitroaromatic permeates into the film. If diffusion of the nitroaromatic into the film is the rate determining step for fluorescence quenching, it is expected that a plot of (fluorescence intensity)$^{-1}$ vs. (time)$^{-1/2}$ will be linear. However, a such plot constructed using the data shown in FIG. 3 is not linear. The deviation from linearity may arise because the concentration of the nitroaromatic at the air-film interface is increasing during the timescale of the experiments.

Additional evidence that the permeation of the analyte in the PTMSDPA film is the most important parameter in determining the fluorescence quenching response time is provided by a study of the time dependence of the fluorescence intensity from a PTMSDPA film for a series of nitroaromatics. Table 1 summarizes the results of a series of experiments where the fluorescence intensity from a 3 nm thick spin-cast PTMSDPA film is monitored as a function of time after being exposed to the vapors of four different nitroaromatic compounds. This data shows that the $t_{50\%}$ response time for the fluorescence quenching process decreases along the series 1,4-DNB>>2,6-DNT>1,3-DNB>>4-NT (see footnote to Table 1 for acronym definitions). Interestingly, the response time correlates strongly with the vapor pressure of the nitroaromatic, i.e., $t_{50\%}$ decreases as the analyte's vapor pressure increases. A similar dependence of the quenching response time on analyte vapor pressure was reported by Yang and Swager in their study of pentiptycene-containing poly-(phenyleneethynylene)s in Yang, J.-S.; Swager, T. M. *J. Am. Chem. Soc.* 1998, 120, 11864–11873, who concluded that permeation of the nitroaromatic vapor into the film was important in establishing the response time of the sensor film.

TABLE 1

| Fluorescence Quenching Response Times[a] | | |
|---|---|---|
| Quencher[b] | Vapor Pressure/ppm in air[c] | $t_{50\%}/s$[d] |
| 1,4-DNB | 0.034 | 880 |
| 2,6-DNT | 0.74 | 48 |
| 1,3-DNB | 1.18 | 21 |
| 4-NT | 210 | 10 |

[a]3 nm PTMSDPA film.
[b]1,4-DNB = 1,4-dinitrobenzene; 2,6-DNT = 2,6-dinitrotoluene; 1,3-DNB = 1,3-dinitrobenzene; 4-NT = 4-nitrotoluene.
[c]From ref.[31]
[d]$t_{50\%}$ is the time required for the PTMSDPA fluorescence intensity to decrease by 50%.

While the response time of the PTMSDPA thin film fluorescence sensor varies strongly with analyte vapor pressure, in general the fluorescence response reaches equilibrium in less than 20 min. FIG. 4 shows the quenching response of 3 nm thick PTMSDPA films to various analytes at t=20 min after exposure to the analyte's vapor. This presentation shows that all of the nitroaromatic compounds tested elicit a significant quenching response from the PTMSDPA film. Interestingly, however, other aromatic compounds such as chloranil, 1,4-dimethoxybenzene (1,4-DMB) and 1,2-dimethoxybenzene (1,2-DMB) give rise to very little quenching (or in the case of 1,2-DMB lead to a slightly enhanced fluorescence intensity). These observations imply that PTMSDPA's quenching response is selective for nitroaromatic compounds. Furthermore, the data support the premise that the mechanism for the fluorescence quenching is charge transfer (CT) complex formation between the electron-rich PTMSDPA chains and the electron poor nitroaromatic residues. It is surprising that chloranil is a poor quencher, despite the fact that it has a relatively high vapor pressure and is a very good electron acceptor. This suggests that specific chemical interactions between the PTMSDPA and the nitroaromatics may be important in determining the strong fluorescence quenching response that is observed.

Figure 5:
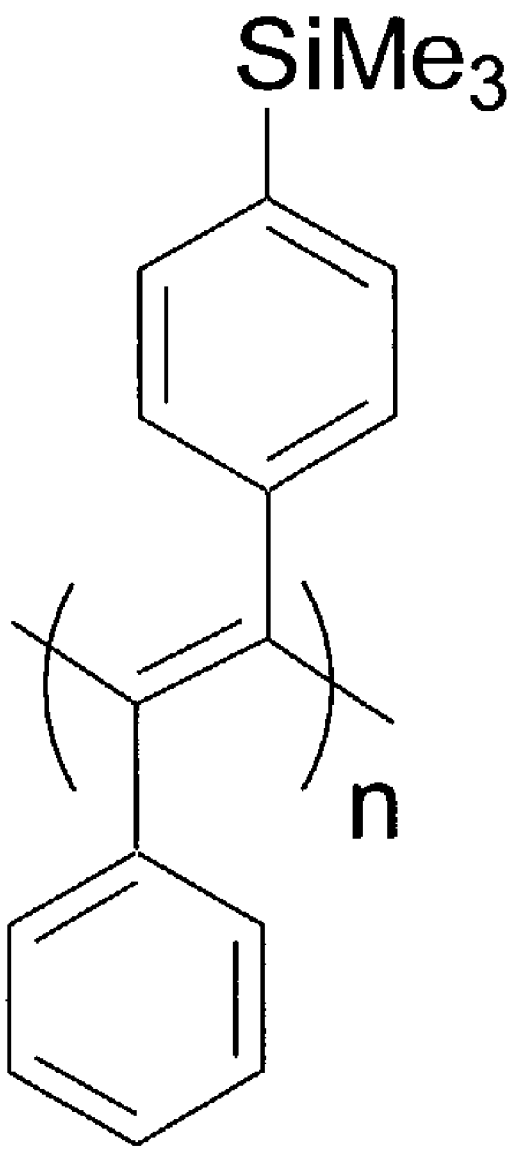
FIG. 5 shows the structure of PTMSDPA.

FIG. 5 shows the structure for PTMSDPA, which can be incorporated with specific embodiments of the subject invention.

Figure 6:
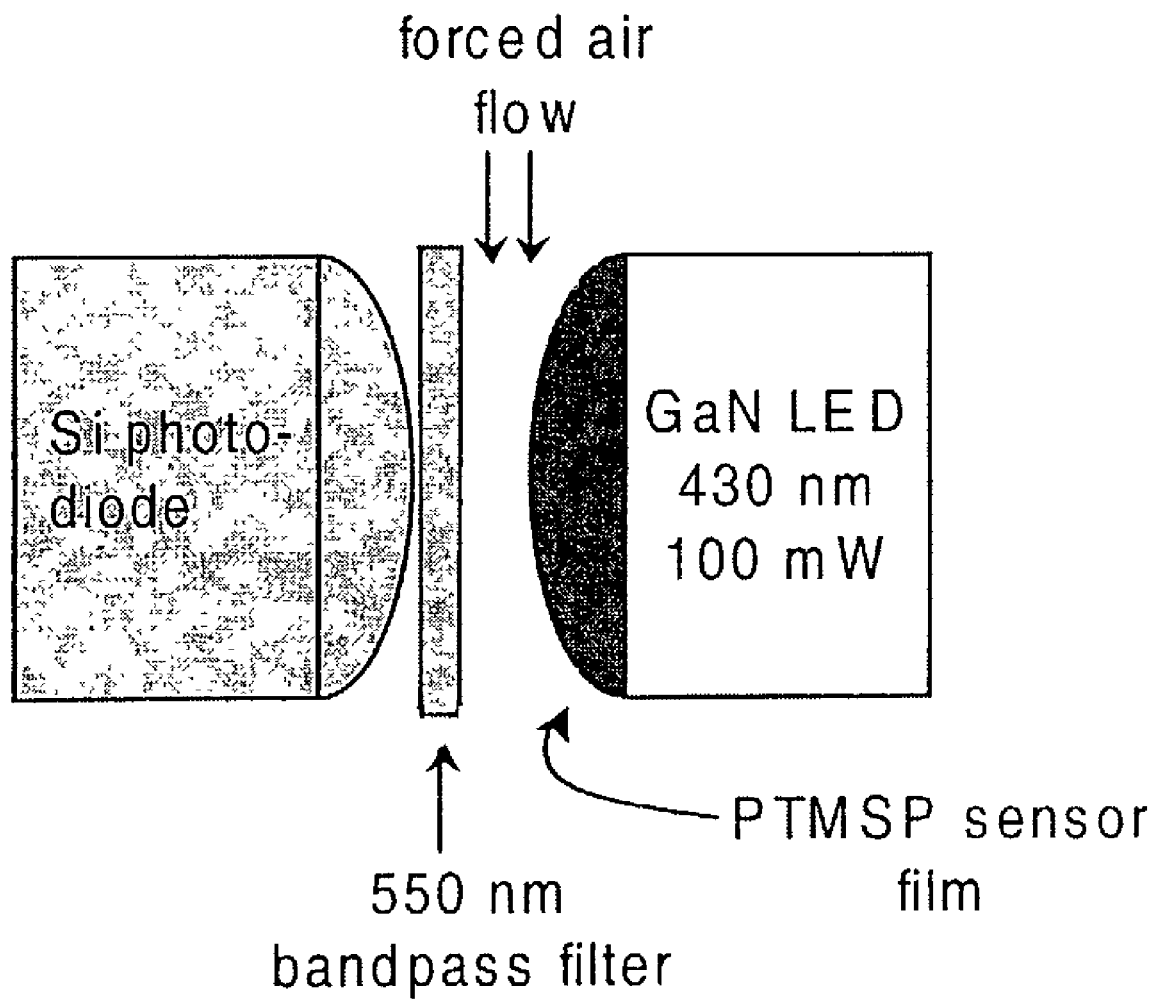
FIG. 6 shows a schematic of a chemical explosives sensor based on PTMSP.

FIG. 6 illustrates a specific embodiment of a detection apparatus in accordance with the subject invention. In this embodiment, a PTMSP sensor film is positioned to receive excitation illumination from an excitation source. In the embodiment shown in FIG. 6, the excitation source is a GaN 430 nm, 100 mW LED and the PTMSP sensor film is positioned adjacent to the output of the LED. The PTMSP sensor film is also positioned to be exposed to a volume of gaseous fluid in which one or more nitroaromatics may be present. In the embodiment, a forced gaseous flow of the volume of gaseous fluid in which one or more nitroaromatics may be present is delivered onto the surface of the PTMSP sensor film. A detector is positioned to measure the luminescence emmitted from the PTMSP sensor film in a wavelength range corresponding to fluorescence from the PTMSP sensor film resulting from the excitation of the film by the LED. In the embodiment, shown in FIG. 6, the detector measures the luminescence emitted from the PTMSP sensor film which passes through a 550 nm bandpass filter, thus measuring the luminescence emitted by the film at wavelengths of about 550 nm. Detection of reduction in luminescence at wavelength of about 550 nm emitted from the film is an indication of the presence of one or more introaromatics in the volume of gaseous fluid.

What is claimed is:

1. A method of detecting the presence of a nitroaromatic, comprising the steps of:
    (a) exposing a luminescent bis-aryl substituted polyacetylene to a volume of a gaseous fluid;
    (b) monitoring the amount of luminescence emitted from the luminescent bis-aryl substituted polyacetylene, and
    (c) monitoring a level of luminescence emitted from the luminescent bis-aryl substituted polyacetylene to determine the presence of a nitroaromatic in the volume of gaseous fluid.

2. The method according to claim 1, wherein the luminescent bis-aryl substituted polyacetylene is fluorescent.

3. The method according to claim 1, wherein the luminescent bis-and substituted polyacetylene is electroluminescent.

4. The method according to claim 1, wherein a fractional free volume of said bis-aryl substituted polyacetylene is 0.26.

5. The method according to claim 1, wherein said monitoring step comprises a user visually monitoring the amount of luminescence emitted from the luminescent bis-aryl substituted polyacetylene.

6. The method according to claim 2, further comprising the steps of:
    exposing the fluorescent bis-aryl substituted polyacetylene to excitation illumination of a wavelength which causes fluorescence from the fluorescent bis-aryl substituted polyacetylene, wherein said monitoring step comprises monitoring the amount of fluorescence emitted from the fluorescent bis-aryl substituted polyacetylene.

7. The method according to claim 3, further comprising the steps of:
exposing the electroluminescent bis-aryl substituted polyacetylene to an electric field which causes electroluminescence from the electroluminescent bis-aryl substituted polyacetylene, wherein said monitoring step comprises monitoring the amount of electroluminescence emitted from the electroluminescent bis-aryl substituted polyacetylene.

8. The method according to claim 1, wherein the luminescent bis-aryl substituted polyacetylene comprises poly-[1-phenyl-2-(4-trimethylsilylphenyl)ethyne].

9. The method according to claim 2, wherein the fluorescent bis-aryl substituted polyacetylene comprises polyacetylene comprises poly-[1-phenyl-2-(4-trimethylsilylphenyl)ethyne].

10. The method according to claim 1, wherein the nitroaromatic is in the vapor-phase.

11. The method according to claim 1, wherein the nitroaromatic is selected from the group consisting of 1,4-dinitrobenzene, 2,4-dinitrotoluene, 2,6-dinitrotoluene, 1,3-dinitrobenzene, 4-nitrotoluene, and 2,4,6-trinitrotoluene.

12. The method according to claim 1, wherein the luminescent bis-aryl substituted polyacetylene is a polymer film.

13. The method according to claim 12, wherein the polymer film is less than 1 micron thick.

14. The method according to claim 12, wherein the polymer film is less than 100 nanometers thick.

15. The method according to claim 12, wherein the thickness of the polymer film is within the range of 3 nanometers to 80 nanometers.

16. The method according to claim 1, wherein the polymer film is less than 10 nanometers thick.

17. The method according to claim 1, wherein the luminescent bis-aryl substituted polyacetylene is an active material in a device which produces an electrical signal, wherein said monitoring step comprises monitoring the electrical signal.

18. The method according to claim 1, wherein the luminescent bis-aryl substituted polyacetylene is in a physical form selected from the group consisting of particles and fibers.

19. The method according to claim 18, wherein the mean diameter of the particles is less than 100 nm.

20. The method according to claim 18, wherein the mean diameter of the fibers is less than 100 nm.

21. The method according to claim 1, wherein said monitoring step comprises monitoring the amount of luminescence emitted from the luminescent bis-aryl substituted polyacetylene with a monitoring means selected from the group consisting of an eye, a photomultiplier, a solid state detector and a charge-couple device (CCD).

22. The method according to claim 6, wherein exposing the fluorescent bis-aryl substituted polyacetylene to excitation illumination comprises exposing the fluorescent bis-aryl substituted polyacetylene to excitation illumination with an illumination means selected from the group consisting of a laser and an LED.

23. The method according to claim 1, wherein the luminescent bis-aryl substituted polyacetylene is substituted with an aromatic moiety.

24. The method according to claim 1, wherein the luminescent bis-aryl substituted polyacetylene is substituted with a heteroaromatic moiety.

25. The method according to claim 1, wherein the luminescent bis-aryl substituted polyacetylene is substituted with a chemical group that contains an aromatic moiety.

26. The method according to claim 1, wherein the luminescent bis-aryl substituted polyacetylene is substituted with a chemical group that contains a heteroaromatic moiety.

* * * * *